US00PP22434P2

(12) United States Plant Patent
Bergman

(10) Patent No.: US PP22,434 P2
(45) Date of Patent: Jan. 3, 2012

(54) ***CHRYSANTHEMUM* PLANT NAMED 'YELLOW YODURANGO'**

(50) Latin Name: *Chrysanthemum×morifolium*
Varietal Denomination: Yellow Yodurango

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,091

(22) Filed: Jun. 18, 2010

(51) Int. Cl.
*A01H 5/00* (2006.01)

(52) U.S. Cl. ..... Plt./289

(58) Field of Classification Search ..... Plt./289
See application file for complete search history.

*Primary Examiner* — Susan McCormick Ewoldt
(74) *Attorney, Agent, or Firm* — S. Matthew Edwards

(57) ABSTRACT

A new *Chrysanthemum* plant named 'Yellow Yodurango' particularly distinguished by the yellow ray floret color, decorative type semi-double flowers, strong stems, good shelf-life, dark green foliage, uniform plant habit and flowering response time, and about an 9-10 week flowering response time.

1 Drawing Sheet

Latin name of the genus and species of the plant claimed: *Chrysanthemum×morifolium.*

Varietal denomination: 'Yellow Yodurango'.

BACKGROUND OF THE NEW PLANT

The present invention comprises a new *Chrysanthemum*, botanically known as *Chrysanthemum×morifolium*, and hereinafter referred to by the variety name 'Yellow Yodurango'.

'Yellow Yodurango' is a product of a planned breeding program. The new cultivar has yellow ray floret color, decorative type semi-double flower, strong stems, good shelf-life, dark green foliage, uniform plant habit and flowering response time, and about an 9-10 week flowering response time.

'Yellow Yodurango' originates as a natural whole plant mutation of 'Yodurango', U.S. Plant Pat. No. 19,736. 'Yellow Yodurango' was discovered and selected by the inventor as a single flowering plant within a population of the parent cultivar in a controlled breeding program in Fort Myers, Fla. in February 2007. The parent cultivar 'Yodurango' has orange-bronze flower color.

The first act of asexual reproduction of 'Yellow Yodurango' was accomplished when vegetative cuttings were propagated from the initial selection in May 2007 in a controlled environment in Fort Myers, Fla.

BRIEF SUMMARY OF INVENTION

Horticultural examination of plants grown from cuttings of the plant initiated in May 2007, and continuing thereafter, has demonstrated that the combination of characteristics as herein disclosed for 'Yellow Yodurango' are firmly fixed and are retained through successive generations of asexual reproduction.

'Yellow Yodurango' has not been observed under all possible environmental conditions. The phenotype may vary significantly with variations in environment such as temperature, light intensity and day length.

A Plant Breeder's Right for this cultivar was applied for in CPVO on Jun. 25, 2009 (#2009/1161). 'Yellow Yodurango' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Yellow Yodurango' with colors being as true as possible with an illustration of this type. The photographic drawing shows 4 flowering potted plants of the new variety growing in a 5½ inch pot and a close-up of the flowers.

DETAILED BOTANICAL DESCRIPTION

The plant descriptions, measurements and aforementioned photographs were taken in Gilroy, Calif. in June 2010 under natural light. These plants were started and grown in Nipomo, Calif. and were shipped to Gilroy in June. Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'YELLOW YODURANGO' AND A SIMILAR VARIETY

| | 'Yellow Yodurango' | 'Yodurango' (U.S. Plant Pat. No. 19,736) |
|---|---|---|
| Petiole length: | Shorter | Longer |
| Ray floret length: | Longer | Shorter |
| Quantity of ray florets: | Fewer | More |
| Quantity of disc florets: | About 25 | None observed |

Plant:
*Form, growth and habit.*—Herbaceous decorative (pot-type). Stems are strong, upright and outwardly spreading, good shelf life, uniform plant habit and flowering response, suitable for production using center budded or no bud.
*Plant height.*—20-23 cm.
*Plant height (inflorescence included).*—25-28 cm.
*Plant width.*—20 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate.
*Immature, leaf color, upper surface.*—Slightly lighter than RHS 147A.
*Lower surface.*—More blue-grey than RHS 147B.
*Mature, leaf color, upper surface.*—Closest to RHS 147A.
*Lower surface.*—More blue-grey than RHS 147B.
*Length.*—9.1-10.0 cm.
*Width.*—5.8-6.1 cm.
*Shape.*—Ovate.
*Base shape.*—Attenuate.
*Apex shape.*—Abruptly acute.
*Margin.*—Palmately lobed, somewhat serrate.
*Texture, upper surface.*—Bi-fid T-shaped hairs.
*Lower surface.*—Bi-fid T-shaped hairs.
*Color of veins, upper surface.*—RHS 144A.
*Color of veins, lower surface.*—RHS 138B.
*Petiole color.*—RHS 144A.
*Length.*—1.7-2.0 cm.
*Diameter.*—0.3-0.4 cm.
*Texture.*—Bi-fid T-shaped hairs.
Stem:
*Quantity of main branches per plant.*—4-6.
*Color of stem.*—RHS 147B.
*Length of stem.*—19-21 cm.
*Diameter.*—0.5 cm.
*Length of internodes.*—1.5-2.0 cm.
*Texture.*—Bi-fid T-shaped hairs.
*Color of peduncle.*—RHS 147B.
*Length of peduncle.*—5-7 cm.
*Peduncle diameter.*—0.3-0.4 cm.
*Texture.*—Bi-fid T-shaped hairs.
Inflorescence:
*Type.*—Composite type, solitary inflorescences (decorative-type) borne terminally above foliage, ray florets arranged acropetally on a capitulum.
*Quantity of short days to flowering (response time).*—About 58-62 days.
*Quantity of inflorescences per plant.*—5-7.
*Lastingness of individual blooms on the plant.*—About 30 days.
*Fragrance.*—Slight.
Bud (just when opening/showing color):
*Color.*—RHS 2A with RHS 5A apex.
*Length.*—1-1.5 cm.
*Width.*—1-1.5 cm.
*Shape.*—Oblate.
Immature inflorescence:
*Diameter.*—About 8.0 cm.
*Color of ray florets, upper surface.*—Starting at RHS 1B and quickly turning RHS 3A but more intense.
*Lower surface.*—RHS 5B.
Mature inflorescence:
*Diameter.*—12-13.5 cm.
*Depth.*—3.0-3.5 cm.
*Total diameter of 'disc'.*—0.4-0.5 cm but is not visible.
*Receptacle height.*—0.6-0.7 cm.
*Receptacle diameter.*—0.8-0.9 cm.
Ray florets:
*Average quantity of florets.*—About 175 in numerous whorls.
*Color of florets, upper surface.*—RHS 3A but more intense.
*Lower surface.*—RHS 5B.
*Length.*—5.1-5.6 cm.
*Width.*—1.4-1.7 cm.
*Shape.*—Elliptical.
*Apex shape.*—Irregularly emarginate.
*Margin.*—Entire.
*Texture, upper surface.*—Papillose.
*Lower surface.*—Papillose.
Disc florets:
*Average quantity of florets.*—About 25.
*Color of florets.*—RHS 24D with RHS 135B apex and RHS 1C basally.
*Length.*—0.35 cm.
*Width.*—0.1 cm.
*Shape.*—Tubular, enlongated.
*Apex shape.*—Acute, 5 pointed.
Phyllaries:
*Quantity.*—About 30.
*Color, upper surface.*—RHS 137B.
*Lower surface.*—Darker than RHS 137A.
*Length.*—1.2-1.3 cm.
*Width.*—0.3-0.4 cm.
*Shape.*—Lanceolate.
*Apex shape.*—Acute.
*Based.*—Fused.
*Margins.*—Entire; papery.
*Texture, upper surface.*—Glabrous.
*Lower surface.*—Bi-fid T-shaped hairs.
Reproductive organs:
*Pistil.*—1, found on both florets.
*Length.*—0.4 cm.
*Style color.*—RHS 1C.
*Style length.*—0.3 cm.
*Stigma color.*—RHS 5A.
*Stigma shape.*—Oval.
*Ovary color.*—Not observed.
*Stamens.*—4, Found on only disc florets.
*Color of filaments.*—RHS 155C.
*Length filaments.*—0.3 cm.
*Anther color.*—RHS 15A.
*Anther length.*—0.1 cm.
*Anther shape.*—Oval.
*Color of pollen.*—Not observed.
*Pollen amount.*—Not observed.
*Fertility/seed set.*—Has not been observed on this hybrid.
Disease/pest resistance: Disease/pest resistance has not been observed on this hybrid.

What is claimed is:

1. A new and distinct variety of *Chrysanthemum* plant named 'Yellow Yodurango' substantially as illustrated and described herein.

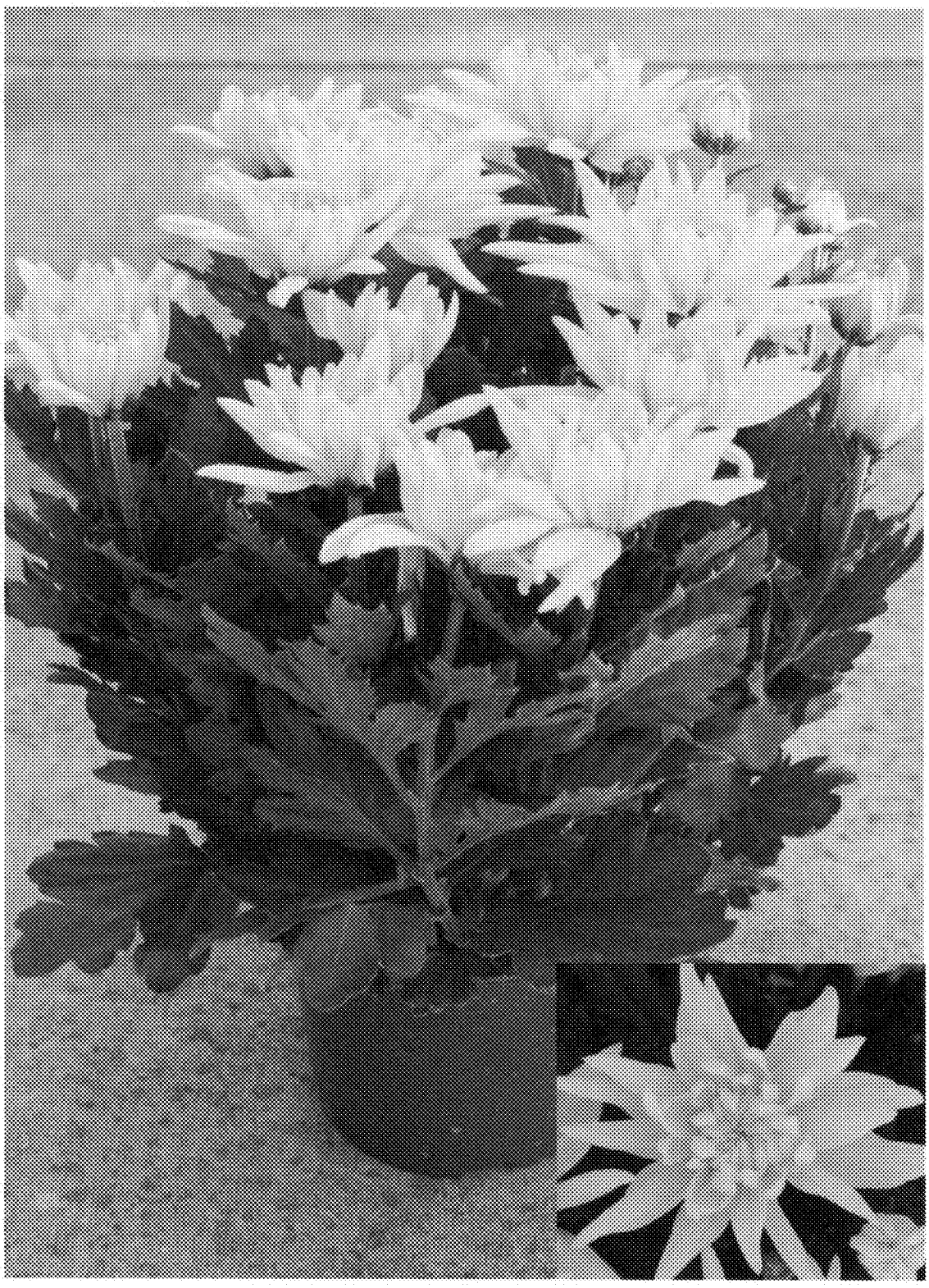

* * * * *